United States Patent
Visser-Luirink et al.

(10) Patent No.: US 6,440,708 B1
(45) Date of Patent: *Aug. 27, 2002

(54) FERMENTATION OF CLAVULANIC ACID AT A CONTROLLED LEVEL OF AMMONIA

(75) Inventors: Gesina Visser-Luirink, Amsterdam; Wilhelmus Theodorus Antonius De Laat, Breda; Jeroen Martijn Klop, Delft, all of (NL)

(73) Assignee: DSM N.V., Te Heerlen (NL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/405,987

(22) Filed: Sep. 27, 1999

Related U.S. Application Data

(60) Provisional application No. 60/118,407, filed on Feb. 2, 1999.

(30) Foreign Application Priority Data

Sep. 29, 1998 (EP) ............................................ 98203314

(51) Int. Cl.⁷ .......................... C12P 17/00; C12P 17/18; C12P 17/14

(52) U.S. Cl. ....................................... 435/117; 119/120
(58) Field of Search ........................... 435/43, 117, 119, 435/120

(56) References Cited

U.S. PATENT DOCUMENTS 5,985,624 A * 11/1999 Valentine et al. ............ 435/119

FOREIGN PATENT DOCUMENTS

| WO | 93/25557 | * 12/1993 |
| WO | 97/39137 | * 8/1997 |
| WO | 98/37179 | * 8/1998 |
| WO | 98/54352 | * 12/1998 |

* cited by examiner

*Primary Examiner*—Sandra E. Saucier
(74) *Attorney, Agent, or Firm*—Morrison & Foerster LLP

(57) ABSTRACT

A method for the production of clavulanic acid by the fermentation of a clavulanic acid producing microorganism at a controlled level of at least 50 mg/l ammonia has been provided for.

Under the application of these reaction conditions surprisingly high production levels of clavulanic acid have been obtained.

8 Claims, No Drawings

FERMENTATION OF CLAVULANIC ACID AT A CONTROLLED LEVEL OF AMMONIA

This application is based on provisional patent application Ser. No. 60/118,407 filed Feb. 2, 1999.

FIELD OF THE INVENTION

The present invention relates to the field of the fermentative production of clavulanic acid by fermentation of a clavulanic acid producing microorganism.

BACKGROUND OF THE INVENTION

Streptomycetes are known to produce a large variety of secondary metabolites which can be applied in the manufacturing of pharmaceuticals. Examples of these pharmaceuticals belong to the classes produced by the Streptomycetes and are for instance polyketides, macrolides, anthracyclines, tetracyclins, lipopeptides and β-lactams, see further Strohl (1997).

One particular example is the production of the β-lactamase inhibitor clavulanic acid, a β-lactam compound which is produced by various microbial strains belonging to the genus of Streptomycetes such as S. clavuligerus ATCC 27064, S. jumonjinensis (GB patent 1563103), S. katsurahamanus IFO 13716 FERM 3944 (JP patent 83009679B) and Streptomyces sp. P6621 FERM 2804 (JP patent application 55162993A).

Secondary metabolism is regulated in various ways in Streptomycetes. Such regulations may comprise the carbon catabolite, ammonium or phosphate repression or any other kind of metabolite that represses the synthesis of the secondary metabolite of interest. Carbon catabolites and ammonium repress the production of cephalosporins in S. clavuligerus (Aharonowitz and Demain 1978 and 1979), nitrogen catabolites regulate the production of spiramycin in S. ambofaciens (Untrau 1994), and phosphate, ammonium and glutamate repress the production of clavulanic acid in S. clavuligerus (Romero et al. 1984). The oxygen concentration influences the regulation of ammonium and phosphate on the antibiotic synthesis by S. clavuligerus (Fang & Demain, 1995). Various types of regulations involved in cephamycin production with various Streptomycetes are described in Omstead et al (1985). High ammonium concentrations were found to repress streptonigrin biosynthesis in S. flocculus (Wallace et al. 1990). A similar negative influence of ammonia on the cefalosporin production by Streptomyces clavuligerus was already described by Aharonowitz and Demain (1979). Furthermore, as S. clavuligerus is urease positive, which urease is repressed by $NH_4Cl$ (see page 2478 of Bascaran et al (1989)) and ureum has been produced during the clavulanic acid production (Elson, 1993), the production of clavulanic acid by S. clavuligerus is described to be especially high when the concentration of ammonium is kept low (WO 96/18743).

However, otherwise than described in the patent application WO 96/18743,surprisingly a large increase in the production of clavulanic acid with a Streptomycete was found when maintaining the ammonium concentration in an optimal rather high concentration range of about minimal 50 mg/l. When this ammonium concentration range was applied, the production of clavulanic acid was improved by more than 20%.

The application of an ammonium concentration of at least 50 mg/l to obtain a surprisingly high yield of clavulanic acid has never been described or suggested in the literature.

SUMMARY OF THE INVENTION

A method has been provided for the production of clavulanic acid by the fermentation of a clavulanic acid producing microorganism on a suitable medium comprising carbon and nitrogen sources wherein during the fermentation of the clavulanic acid producing mircoorganism the concentration of ammonia is maintained equal to or higher than 50 mg/l, particularly equal to or higher than 75 mg/l, more particularly equal to or higher than 100 mg/l. The concentration of ammonium is regulated by applying one or two of the measures selected from regulation of the rate of ammonium addition, for instance ammonium sulfate or urea or regulation of the addition of one or more ammonium containing titrants selected from ammonia and ammonium hydroxide, combined for instance with sulfuric acid and sodium hydroxide. Preferably the pH during this fermentation has been maintained between 6.5 and 7.5 and preferably the fermentation is carried out in a fed batch, continuous or semi-continuous mode.

DETAILED DESCRIPTION OF THE INVENTION

According to the present invention it was surprisingly found that when the ammonium concentration is maintained equal to or higher than 50 mg/l, particularly equal to or higher than 75 mg/l and more particularly equal to or higher than 100 mg/l, the clavulanic acid production is largely improved compared to a fermentation process where the ammonium concentration is kept low (<50 mg/l). By using fed batch fermentation techniques known in the art, nutrients can be fed to an industrial fermentor in order to provide the optimal physiological conditions with the aim to maximize output from a given fermentation process. As an example, the residual ammonium concentration in a fermentation broth can be controlled at the desired concentration range by adding an ammonium source continuously or discontinously (intermittently) to the fermentor. This can be done either directly by manipulating the flow of the nitrogen source (ammonium, ammonium salts like ammonium chloride, ammonium nitrate, ammonium phosphate and ammonium carbonate or urea as an ammonium precursor), or indirectly by adding ammonium as an alkaline titrant, eventually alternating with sodium hydroxide in order to prevent excess ammonium dosage. Furthermore, the ammonium concentration can be reduced for instance by manipulation of the temperature or pH, which leads to an increased growth rate and an increased ammonium consumption rate. The ammonium concentration can be controlled by adjusting the flow of the nitrogen source or by manipulation of the alkaline titrant and/or the pH.

According to the present invention the ammonium concentration is maintained equal to or higher than 50 mg/l. On the other hand, the ammonium concentration must be low enough for reducing the repression of secondary metabolism and avoiding toxicity of ammonium. For instance, the ammonium concentration could be maintained below 2500 mg/l, preferably 1000 mg/l, for instance 500 mg/l.

The microorganism used for production of clavulanic acid may be any Streptomycete, optionally improved for growth and/or clavulanic acid production by means of classical strain improvement or by recombinant DNA techniques, for instance S. clavuligerus or S. jumonjinensis.

The production of clavulanic acid is carried out by fermentation of a Streptomycete on a suitable medium comprising various carbon and energy sources like sugars such as glucose, fructose, sucrose, maltose, lactose, or polysaccharides like starch, maltodextrines and inuline or other fructose polymers, proteins such as flours from nuts, vegetables, seeds, cereals, grasses such as those useful in fermentation industry; soybean flour, lineseed flour, peanut flour, potato flour, sunflower, pea- or beanflour, cotton seed flour, wheat gluten, whole wheat, rice meal, or proteins derived from animal sources called peptones, or proteins derived from microbial sources like yeast extracts, triglycerides such as soybean oil, sunflower oil, olive oil, tri-oleate etc., (poly-) alcohols such as ethanol, propanol, glycerol, mannitol, or organic acids or a salt thereof such as acetate, propionate, succinate, adipate, malonate, fumarate, citrate, lactate, gluconate etc. and nitrogen sources such as ammonium salts, ammonium, urea, nitrate, asparagine, aspartate, glutamate, lysine and from complex sources such as protein products derived from microbial source (yeast extract) or plants (corn steep liquor, soybean flour, cotton seed flour etc.) and animals (peptones). Phosphor is either supplied in the form of an inorganic salt, or as a phosphor protein like casein, or bound to inositol in the form of phytate as present in many plant protein sources like soybean flour or bound in nucleotides as present in yeast extracts.

Further vitamins and various sorts of inorganic anions such as sulphates, phosphates, chlorides, borates, molybdate, iodate and inorganic cations such as potassium, sodium, zinc, manganese, magnesium, iron, copper, cobalt, nickel may be added to the fermentation medium.

A fermentation is started by inoculating from a preculture or inoculum fermentation at a volume of 1 to 50% of the main fermentation medium, particularly from 5 to 20%. The process may last from 24 to 400 hours and especially from 48 to 168 hours. The temperature will be kept between 20 and 40° C., in particular between 25 and 35° C., and even more particular between 25 and 30° C. The pH should be maintained preferably at pH 6 to 8, more preferably between pH 6.5 and 7.5 by means of titration with an alkaline substance such as ammonia, sodium hydroxide, potassium hydroxide, calcium hydroxide, or an organic base like lysine, arginine and histidine or a combination of these alkaline substances and an acid substance, such as the inorganic acids like sulphuric acid, hydrochloric acid, phosphoric acid and nitric acid. Alternatively, an organic acid may be used such as glutamate, citrate, gluconate or acetate.

The dissolved oxygen concentration is preferably controlled in the optimal range for the process by varying one or more of the following parameters: the oxygen concentration in the inlet gas, application of overpressure, modification of stirrer speed or airflow. The range may vary between 0 and 100% of air saturation.

Carbon dioxide should be kept at non-toxic concentrations by increasing the airflow through the fermentor so that the carbon dioxide concentration in the outlet-gas is less than 5%, more particular less than 2.5%.

The fermentation can be carried out in a batch, a fed batch, or a continuous fermentation process mode.

The process may be carried out by controlling various non-growth limiting nutrients in their optimal concentrations. Dependent on the growth limiting nutrient of choice, these growth-non-limiting nutrients may contain any relevant source of carbon, nitrogen, phosphor or sulphur or may contain oxygen.

Of course, the recovery of the impure clavulanic acid solution as formed by the fermentative process of the present invention as well as the subsequent conversion thereof into a pharmaceutically acceptable salt by methods known in the art do form an aspect of the present invention. One of the most advantageous procedures is the conversion of the impure clavulanic acid into an amino salt thereof by adding the corresponding amino salt forming compound as for instance N,N,N', N'-tetramethylethylenediamine, 1,3-bis(dimethylamino)-2-propanol, t-butylamine, t-octylamine, benzhydrylamine and bis (2-( dimethyl-amino)ethyl)ether and reacting said amine clavulanate with a non-toxic pharmaceutically acceptable salt as for instance potassium ethylhexanoate to form the corresponding purified salt, for instance potassium clavulanate.

The following examples are only to be considered as illustration of the present invention.

REFERENCES

Strohl W. R., Biotechnology of Industrial Antibiotics, Marcel Dekker Inc., page 1–48 (1997).
Aharonowitz Y. and Demain A. L., Antimicrobial Agents and Chemotherapy Vol. 14, No. 2, pages 159–164 (1978).
Aharonowitz Y. and Demain A. L., Can. J. Microbiol. 25, 61–67 (1979).
Aharonowitz Y. and Friedrich C. G., Arch. Microbiol. 125, 137–142 (1980).
Elson S. W., Baggaley K. H., Davidson M., Fulston M., Nickolson N. H., Risbridger, G. D. and Tyler, J. W., J. Chem. Soc., Chem. Commun. 1213 (1993).
Butterworth, Biotechnology of Industrial Antibiotics, Marcel Dekker Inc., pages 225–235 (1984).
Romero J. Liras P. and Martin J. F., Appl. Microbiol. Biotechnol. 20, 318–325 (1984).
Omstead D. R., Hunt G. R. and Buckland B. C. in Comprehensive Biotechnology Pergamon Press, Vol. 3, Edited by Harvey W. Blanch, Stephen Drew and Daniel I. C. Wang, pages 187–210 (1985).
Brana A. F., Paiva N. and Demain A. L., J. of Gen. Microbiol. 132, 1305–1317 (1986).
Brana A. F., Wolfe S. and Demain A. L., Arch. Microbiol. 146, 46–51 (1986).
Bascaran V., Hardisson C. and Brana A. F., J. of General Microbiology 135, 2465–2474 (1989).
Bascaran V., Hardisson C. and Brana A. F., J. of General Microbiology 135, 2475–2482 (1989).
Wallace K. K., Payne G. F. and Speedie M. K., J. of Industrial Microbiology, 6, 43–48 (1990).
Untrau S., Lebrihi A., Lefebvre G. and Germain P., Curr. Microbiol. 28 (1994).
Kasarenini S. and Demain A. L., J. of Industrial Microbiology 13, 217–219 (1994).
Fang A. and Demain A. L., J. of Industrial Microbiology 15, 407–410 (1995).

EXAMPLE 1

*Streptomyces clavuligerus* ATCC27064 was improved for clavulanic acid production by means of several rounds of classic mutation (UV, nitroso guanidine (NTG)) and selection in shake flask cultures whereby clavulanic acid production was tested by imidazole methods as known in the art. The strain was conserved as vegetative mycelium grown for 48 hours in Tryptone Soytone Broth-medium (TSB-medium) at 28° C. in a shaker incubator shaken at 280 rpm and stored frozen at −80° C.

1 ml of the frozen mycelium was inoculated to 100 ml of a sterilized (30 minutes, 121° C.) preculture medium containing 5–20 g/l maltose. 1 aq, 15–30 g/l bacto tryptone, 15–30 g/l bacto peptone, 1–10 g/l bacto soytone, mono potassium phosphate (1–5 g/l) and 0.2 g/l synthetic antifoam.

After 72 hours of cultivation at 27° C., 100 ml of the culture is transferred to the inoculum fermentor with 70 l of steam-sterilized medium at pH 7 containing glycerol (20–50 g/l), soybean flour (20–40 g/l), casein hydrolysate (10–50 g/l), mono potassium phosphate (2–5 g/l), a suitable trace element cocktail and synthetic antifoam (1 g/l). The inoculum fermentation medium was again grown for 72 hours at 26–30° C. keeping the dissolved oxygen concentration above 25% of air saturation by increasing airflow, agitation and backpressure if required.

The main fermentation is inoculated by transferring 9 l of the inoculum broth to the main fermentor by pressurizing the inoculum fermentor containing 150 l medium sterilized by steam prior to inoculation. The medium contained glycerol (50–100 g/l), soybean flour (5–20 gl), casein hydrolysate (10–50 g/l), mono potassium phosphate (0.5–2 g/l), a suitable trace element cocktail and synthetic antifoam (0.2–2 g/l).

The pH was maintained at 7 +/−0.25 by titration with NaOH and sulphuric acid while the temperature was kept between 26 and 29° C. by pumping cooling water through the jackets of the fermentor. The dissolved oxygen concentration was kept above 25% of air saturation by increasing airflow, backpressure and stirrer speed if required.

In case of ammonium controlled fermentations, 0.58 g/l of ammonium sulphate was added to the main fermentation medium after sterilisation and ammonium was fed to the fermentor using a sterile diluted solution of the same containing 12 g/l $NH_3$ as sulphate salt. The flow was adjusted to get the ammonium at the desired concentration range upon off-line measurement of the concentration of ammonium every 2 hours. When the concentration of ammonium in the broth got higher than 500 mg/l, the pH was increased by addition of an alkaline titrant with 0.2 unit in order to reduce the ammonium concentration under that level.

In table 1 we see that when the ammonium concentration was controlled above 50 mg/l, the clavulanic acid production was increased with more than 25% in two independent runs. During the reference fermentation experiment ammonium has been below 50 mg/l for 35 hours; between 5 and 40 hours after inoculation. After this period ammonium rises due to clavulanic acid production.

TABLE 1

Experimental results of clavulanic acid-fermentations on a 300 l scale with and without ammonium control.

| Experiment | Relative Titer |
| --- | --- |
| Reference example without ammonium control | 100% |
| Ammonium controlled example 1 | 132% |
| Ammonium controlled example 2 | 127% |

What is claimed is:

1. A method for the production of clavulanic acid comprising regulating the concentration of ammonium ion during fermentation of a clavulanic acid producing microorganisms on a suitable medium comprising carbon and nitrogen sources wherein the concentration of ammonium ion is maintained from 100 mg/l to 2,500 mg/l by regulating the rate of ammonium ion addition and/or regulating the addition of at least one titrant for ammonium ion.

2. The method according to claim 1, wherein the ammonium ion addition is the addition of ammonium sulfate or urea.

3. The method according to claim 1, wherein the at least one titrant is selected from the group consisting of ammonia and ammonium hydroxide, combined with sulfuric acid and optionally sodium hydroxide.

4. The method of claim 1 wherein the pH is maintained between 6.5 and 7.5.

5. The method of claim 1 wherein the fermentation is carried out in a fed batch, continuous or semi-continuous mode.

6. The method of claim 1 further comprising recovering the clavulanic acid.

7. The method of claim 6, further comprising converting the recovered clavulanic acid into an amine salt thereof by adding the corresponding amine salt forming compound thereto and reacting said amine clavulanate with a non-toxic, pharmaceutically acceptable salt, and purifying the salt of clavulanic acid.

8. The method of claim 6, further comprising purifying the recovered clavulanic acid.

* * * * *